(12) United States Patent
Peets

(10) Patent No.: US 11,295,629 B1
(45) Date of Patent: Apr. 5, 2022

(54) FAUCET COMPRISING INTEGRATED DETECTION MECHANISMS AND METHODS OF MAKING AND USING THE SAME

(71) Applicant: Risa Peets, Greensboro, NC (US)

(72) Inventor: Risa Peets, Greensboro, NC (US)

( * ) Notice: Subject to any disclaimer, the term of this patent is extended or adjusted under 35 U.S.C. 154(b) by 0 days.

(21) Appl. No.: 17/398,424

(22) Filed: Aug. 10, 2021

(51) Int. Cl.
*G09B 19/00* (2006.01)
*E03C 1/04* (2006.01)
*E03C 1/05* (2006.01)

(52) U.S. Cl.
CPC .......... *G09B 19/0076* (2013.01); *E03C 1/04* (2013.01); *E03C 1/057* (2013.01)

(58) Field of Classification Search
CPC ... G01F 13/006; G09B 19/0076; E03C 1/057; E03C 1/04
USPC .......................................................... 4/668
See application file for complete search history.

(56) References Cited

U.S. PATENT DOCUMENTS

| | | | | |
|---|---|---|---|---|
| 4,502,164 A | * | 3/1985 | Gemmell | A61L 2/04 422/106 |
| 4,606,085 A | * | 8/1986 | Davies | A61B 90/80 4/619 |
| 5,287,570 A | * | 2/1994 | Peterson | E03C 1/052 4/668 |
| 5,845,844 A | * | 12/1998 | Zosimodis | E03C 1/057 236/12.12 |
| 5,966,753 A | | 10/1999 | Gauthier et al. | |
| 5,975,124 A | * | 11/1999 | Stevens, II | E03C 1/05 68/12.22 |
| 5,979,776 A | * | 11/1999 | Williams | G05D 23/1393 236/12.12 |
| 6,059,192 A | * | 5/2000 | Zosimadis | E03C 1/057 236/12.12 |
| RE37,888 E | * | 10/2002 | Cretu-Petra | E03C 1/057 236/12.12 |
| 7,228,874 B2 | * | 6/2007 | Bolderheij | E03C 1/055 222/145.5 |

(Continued)

OTHER PUBLICATIONS

Tafton, "New sensors can detect single protein molecules", Jan. 2017, MIT News (https://news.mit.edu/2017/new-sensors-detect-single-protein-molecules-0123) (Year: 2017).*

(Continued)

*Primary Examiner* — Benjamin R Shaw
(74) *Attorney, Agent, or Firm* — Ashley D. Johnson; Dogwood Patent and Trademark Law

(57) ABSTRACT

The presently disclosed subject matter is generally directed to a faucet that includes one or more integrated detection mechanisms to decrease or eliminate the incidence of healthcare associated infections. Specifically, the disclosed faucet a includes timing sensor that is activated by the user to ensure that the user washes their hands for the appropriate amount of time. The faucet further includes a thermal sensor positioned within the interior of the faucet neck that detects the temperature of the water flowing through the faucet. Optionally, the faucet can include an additional internal sensor that the detects the presence of one or more harmful proteins. In this way, the faucet promotes efficient hand washing techniques, as well as provides information on the condition of the water to track harmful bacteria (e.g., legionella) growth.

20 Claims, 7 Drawing Sheets

(56) References Cited

U.S. PATENT DOCUMENTS

| | | | |
|---|---|---|---|
| 7,819,136 B1* | 10/2010 | Eddy | G01F 11/00 137/624.11 |
| 8,316,883 B1* | 11/2012 | Watson | E03C 1/0404 137/551 |
| 8,438,672 B2 | 5/2013 | Reeder et al. | |
| 9,266,136 B2* | 2/2016 | Klicpera | B05B 12/02 |
| 9,526,380 B2* | 12/2016 | Hamilton | G08B 21/245 |
| 9,721,452 B2 | 8/2017 | Felch et al. | |
| 10,489,038 B2 | 11/2019 | Klicpera | |
| 10,874,761 B2 | 12/2020 | Riggio et al. | |
| 2003/0010721 A1* | 1/2003 | Aldred | E03C 1/04 210/85 |
| 2009/0106891 A1* | 4/2009 | Klicpera | G01F 15/063 4/605 |
| 2009/0293189 A1* | 12/2009 | Somerville | G01K 13/02 4/597 |
| 2011/0186154 A1* | 8/2011 | Klicpera | B67D 7/08 137/551 |
| 2011/0210276 A1* | 9/2011 | Chen | G05D 23/193 251/129.01 |
| 2012/0101879 A1 | 4/2012 | Galakatos et al. | |
| 2013/0340162 A1* | 12/2013 | Peel | E03C 1/0404 4/676 |
| 2014/0352799 A1* | 12/2014 | Rosko | C02F 1/78 137/237 |
| 2015/0376880 A1* | 12/2015 | Chen | G05D 23/1927 4/668 |
| 2017/0294106 A1* | 10/2017 | Thyroff | G10L 17/00 |
| 2018/0121951 A1* | 5/2018 | Boey | E03C 1/057 |
| 2020/0393456 A1* | 12/2020 | Alexandrakis | G01N 21/648 |
| 2021/0259552 A1* | 8/2021 | Dacosta | G01N 21/6456 |

OTHER PUBLICATIONS

Dalton, "Researchers design sensors that can detect single protein molecules", Jan. 2017, Engadget (https://www.engadget.com/2017-01-25-mit-researchers-single-protein-molecule-sensors.html) (Year: 2017).*

* cited by examiner

FAUCET COMPRISING INTEGRATED DETECTION MECHANISMS AND METHODS OF MAKING AND USING THE SAME

TECHNICAL FIELD

The presently disclosed subject matter is generally directed to a faucet comprising one or more integrated detection mechanisms. For example, the faucet is capable of measuring the temperature of water that passes through the system, initiating a timer, and detecting the amount of one or more bacterial proteins in the water. The presently disclosed subject matter further includes methods of making and using the faucet.

BACKGROUND

The transmission of healthcare-associated infections (HAI) among patients remains a notable concern for healthcare systems. Particularly, the Center for Disease Control (CDC) estimates that one in 31 hospitalized patients acquire at least one HAI, which potentially lengthens patient hospital stays and increases overall cost for hospital systems. However, effective hand hygiene has been identified as the single most effective way to mitigate germs and their transmission within healthcare settings. Proper and effective hand washing procedure typically requires hands to be washed with soap and water for twenty seconds or longer. While this is a well understood requirement, adherence is often poor. Unfortunately, studies show that on average, only a small subset of healthcare, food preparation, and other individuals requiring high standards of hygiene actually wash their hands as long as they should. In particular, most people do not wash for the recommended twenty seconds, and many people wash for less than ten seconds, a time that is insufficient for proper cleaning.

In addition, germs that cause HAIs can also be transmitted via other modes. For example, the bacterium legionella is commonly present in water environments, and has been identified as a leading cause of legionellosis. Legionellosis includes serious conditions, such as Legionnaires' disease and Pontiac fever. Large water systems (including hospital water systems) have been identified by the CDC as having favorable environmental conditions for legionella growth. The estimated cost of legionellosis in the United States totals 433 million per year (United States Environmental Protection Agency, 2016). Mitigating the growth of legionella is therefore an ongoing priority for healthcare systems.

It would therefore be beneficial to provide a device that facilitates proper handwashing techniques, while also detects the presence of harmful bacteria in the water system.

SUMMARY

In some embodiments, the presently disclosed subject matter is directed to a faucet. Particularly, the faucet includes a neck defined by an interior passageway configured to allow the flow of water therethrough and an outlet through which water exits the faucet. The faucet further includes a timing sensor triggered by a user's approach to the faucet, and a timer configured to run for a predetermined amount of time, wherein the timer is initiated by the triggering of the timer sensor.

In some embodiments, the timer sensor is selected from one or more motion sensors, heat sensors, light sensors, and/or voice activated sensors.

In some embodiments, the predetermined amount of time is about 20 seconds.

In some embodiments, the timer provides a visual countdown, an audible countdown, or both.

In some embodiments, the timer provides an indicator to the user when the predetermined amount of time has elapsed.

In some embodiments, the faucet further includes one or more thermal sensors configured to detect the temperature of water passing through the interior passageway of the neck.

In some embodiments, the faucet includes a visible light fluorescence spectrometer element configured to illuminate the area below the faucet output with blue visible light, thereby illuminating one or more microbial contaminants on an object positioned below the faucet output.

In some embodiments, the thermal sensor is selected from one or more infrared sensor, thermistor, thermocouple, diode sensor, or resistance temperature detector.

In some embodiments, the one or more thermal sensors are initiated by the presence of water, the timing sensor, or both.

In some embodiments, data produced by the thermal sensor is transmitted to a central processing center.

In some embodiments, the faucet includes one or more protein sensors configured to detect single protein molecules of bacteria.

In some embodiments, the bacteria is legionella.

In some embodiments, the faucet further comprises one or more lights that are initiated by the triggering of the timing sensor.

In some embodiments, the faucet further comprises one or more transmitters that project an audible message, initiated by the triggering of the timing sensor.

In some embodiments, the presently disclosed subject matter is directed to a method of indicating to a user the proper amount of time to wash their hands. Particularly, the method comprises initiating the timing sensor of the disclosed faucet. The method further includes initiating water flow from the faucet outlet, whereby the user washes their hands until the timer indicates that a predetermined time has elapsed.

In some embodiments, the presently disclosed subject matter is directed to a method of reducing the incidence legionella-related illness. Particularly, the method comprises tracking the temperature of water dispensed from the disclosed faucet monitor temperatures favorable for the growth of legionella. The method includes tracking the amount of legionella-indicative protein present in the water to monitor the presence of legionella and/or comparing the amount of legionella protein present to a threshold limit, whereby the incidence of legionella-related infection or illness is reduced.

In some embodiments, a notification is provided if the temperature of the water is favorable for the growth of legionella, if the presence of legionella in the water reaches the threshold limit, or both.

In some embodiments, the faucet is inoperable if the temperature of the water is favorable for the growth of legionella or if the presence of legionella in the water reaches the threshold limit.

DETAILED DESCRIPTION

Figure 1:
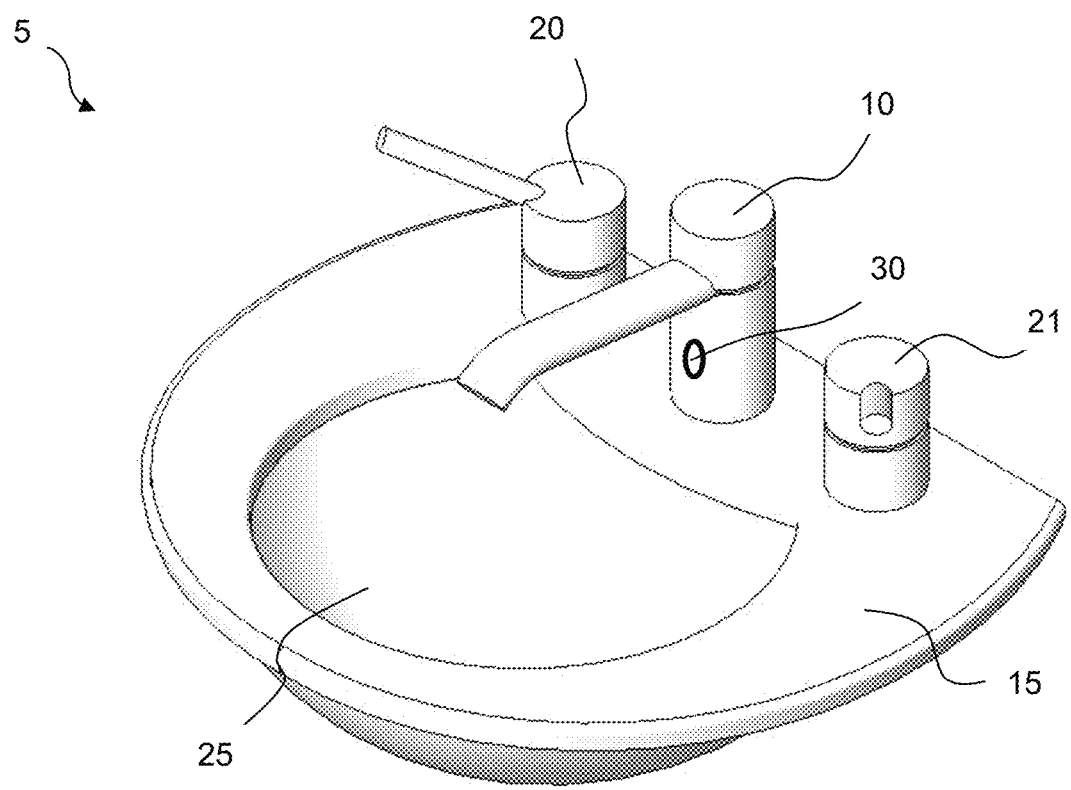
FIG. 1 is a perspective view of a sink design comprising a faucet in accordance with some embodiments of the presently disclosed subject matter.

The presently disclosed subject matter is introduced with sufficient details to provide an understanding of one or more particular embodiments of broader inventive subject matters. The descriptions expound upon and exemplify features of those embodiments without limiting the inventive subject matters to the explicitly described embodiments and features. Considerations in view of these descriptions will likely give rise to additional and similar embodiments and features without departing from the scope of the presently disclosed subject matter.

Unless defined otherwise, all technical and scientific terms used herein have the same meaning as commonly understood to one of ordinary skill in the art to which the presently disclosed subject matter pertains. Although any methods, devices, and materials similar or equivalent to those described herein can be used in the practice or testing of the presently disclosed subject matter, representative methods, devices, and materials are now described.

Following long-standing patent law convention, the terms "a", "an", and "the" refer to "one or more" when used in the subject specification, including the claims. Thus, for example, reference to "a device" can include a plurality of such devices, and so forth. It will be further understood that the terms "comprises," "comprising," "includes," and/or "including" when used herein specify the presence of stated features, integers, steps, operations, elements, and/or components, but do not preclude the presence or addition of one or more other features, integers, steps, operations, elements, components, and/or groups thereof.

Unless otherwise indicated, all numbers expressing quantities of components, conditions, and so forth used in the specification and claims are to be understood as being modified in all instances by the term "about". Accordingly, unless indicated to the contrary, the numerical parameters set forth in the instant specification and attached claims are approximations that can vary depending upon the desired properties sought to be obtained by the presently disclosed subject matter.

As used herein, the term "about", when referring to a value or to an amount of mass, weight, time, volume, concentration, and/or percentage can encompass variations of, in some embodiments+/−20%, in some embodiments+/−10%, in some embodiments+/−5%, in some embodiments+1-1%, in some embodiments+/−0.5%, and in some embodiments+/−0.1%, from the specified amount, as such variations are appropriate in the disclosed packages and methods.

As used herein, the term "and/or" includes any and all combinations of one or more of the associated listed items.

Relative terms such as "below" or "above" or "upper" or "lower" or "horizontal" or "vertical" may be used herein to describe a relationship of one element, layer, or region to another element, layer, or region as illustrated in the drawing figures. It will be understood that these terms and those discussed above are intended to encompass different orientations of the device in addition to the orientation depicted in the drawing figures.

The embodiments set forth below represent the necessary information to enable those skilled in the art to practice the embodiments and illustrate the best mode of practicing the embodiments. Upon reading the following description in light of the accompanying drawing figures, those skilled in the art will understand the concepts of the disclosure and will recognize applications of these concepts not particularly addressed herein. It should be understood that these concepts and applications fall within the scope of the disclosure and the accompanying claims.

The presently disclosed subject matter is generally directed to a faucet that includes one or more integrated detection mechanisms to decrease or eliminate the incidence of healthcare associated infections. The term "faucet" as used herein broadly refers to any valve and associated discharge pipe that draws water from a source or reservoir and discharges the drawn water. FIG. 1 illustrates one embodiment of sink assembly 5 comprising faucet 10 mounted on sink deck 15. The assembly also includes first and second handles 20, 21 configured to dispense hot and cold water, respectively. The sink assembly includes basin 25 that connects with the bathroom or kitchen plumbing to recycle or dispose of the used water. Faucet 10 includes timing sensor 30 that is activated by the user to initiate a timer to ensure that the user washes their hands for the appropriate amount of time. Faucet 10 further includes a temperature sensor positioned within the interior of the faucet neck that detects the temperature of the water flowing through the faucet. Optionally, the faucet can include an additional internal sensor that the detects the presence of one or more harmful proteins, such as those indicative of legionella. In this way, faucet 10 promotes efficient hand washing techniques, as well as provides information on the condition of the water to track harmful bacteria (e.g., legionella) growth. It should be appreciated that the sink assembly 5 can take any desired form and is not limited to the embodiment shown in FIG. 1.

Figure 2A:
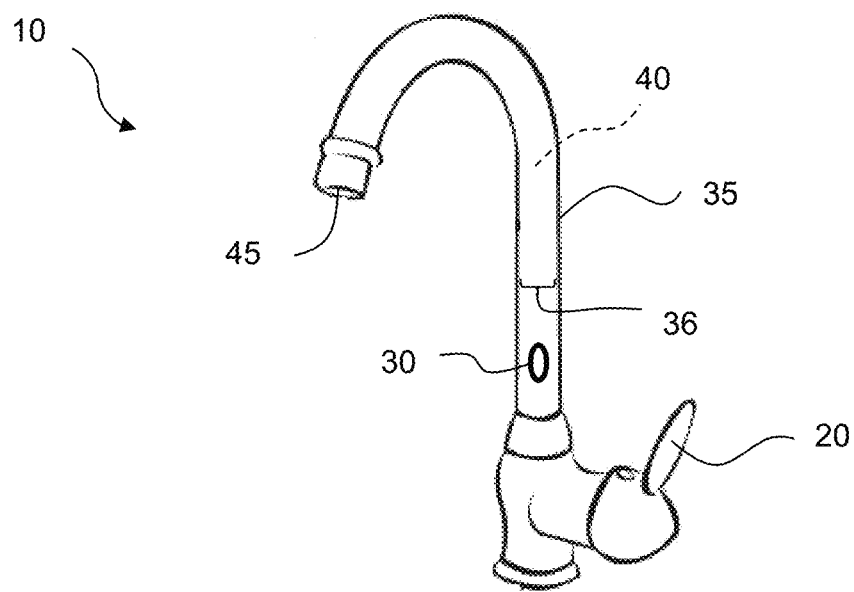
FIG. 2a is a perspective view of a faucet comprising a timing sensor in accordance with some embodiments of the presently disclosed subject matter.

FIG. 2a illustrates one embodiment of faucet 10 comprising elongated neck 35 with internal passageway 40 through which water can flow. The faucet neck can have any desired length (e.g., the distance spanning each end of the neck) such as about 1-20 inches or more. Faucet neck 35 can have any desired thickness 36, such as about 0.5-3 inches or more. The faucet neck can further have any desired shape, such as the hooked shape of FIG. 2a, or a straight, angled, rounded, or abstract shape. Neck 35 can have any cross-sectional shape, such as round, oval, square, rectangular, triangular, abstract, and the like.

Faucet 10 includes outlet 45 through which water dispensed, such as to wash a user's hands. Optionally, one or more handles 20 can be positioned adjacent to the faucet to turn the water on/off and/or adjust the temperature of the water. However, the presently disclosed subject matter is not limited and the faucet can be touchless, requiring no handles.

Faucet 10 can be constructed from any desired material, such as (but not limited to) metal (e.g., stainless steel, bronze, copper, steel, galvanized steel), ceramics, plastic (polyvinyl chloride, polyethylene, polybutylene, polypropylene), and the like. In some embodiments, the faucet can include any desired coating, such as any of a wide variety of colors, finishes, and other decorative elements.

Figure 2B:
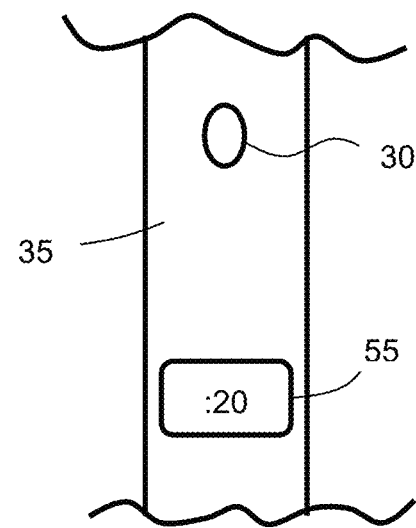
FIG. 2b is a fragmentary front plan view of a faucet comprising a sensor and a timer in accordance with some embodiments of the presently disclosed subject matter.

As illustrated in FIG. 2b, the disclosed faucet includes timing sensor 30 positioned on an external surface of the faucet, such as the neck. The term "timing sensor" refers to any detecting, monitoring, or controlling device that is capable of activating or deactivating an associated timer. Thus, timing sensor 30 can include any type of sensor that is triggered when a user approaches the faucet. For example, timing sensor 30 can be a motion sensor, heat sensor, light sensor, and/or voice activated sensor. Thus, in some embodiments, the timing sensor can include a light source (e.g., an infrared emitter configured to detect motion) that is triggered when the light is interrupted, such as by a user approaching the faucet. However, timing sensor 30 is not limited and any triggering mechanism can be used.

The timing sensor can be positioned on any surface of faucet 10. Typically, the timing sensor will be positioned on the front side of the faucet neck (e.g., facing the user when the faucet is in use). In this way, sensor 30 can detect the presence of a user, such as when the user approaches the faucet and/or places his or her hands under the faucet. However, it should be appreciated that the location of timing sensor 30 is not limited.

Although a single timing sensor is illustrated in the Figures, it should be appreciated that faucet 10 can include any number of sensors 30 (e.g., 1-10) that cooperate to detect when a user is nearby.

When the timing sensor is triggered, timer 55 is activated. The timer can be set with a predetermined amount of time (e.g., 20 seconds, 30 seconds, etc.). In some embodiments, the timer is set for the optimal time suggested for hand washing with soap and water. Timer 55 can be configured within the faucet neck itself or attached to the external surface of the neck using any conventional mechanism (e.g., welding, adhesive, magnets, and the like). The timer can be positioned at any location along the faucet, such as above, below, or beside timing sensor 30. Each time the sensor is triggered, the timer will begin counting down. In some embodiments, the timer is capable of producing an audible countdown instead of (or in addition to) the visual countdown.

Timer 55 provides a visual countdown for the user, allowing the user to see the exact amount of time they have spent washing their hands. In some embodiments, the timer can include a small video screen that can be used to display images and/or video. For example, the timer can include words or video showing users proper hand washing techniques. The video content can be preloaded or transmitted to the timer display in real time.

When the timer completes the countdown, it is an indication to the user that they have spent an appropriate amount of time washing their hands. In some embodiments, the when the timer fully counts down, an auditory tone is produced (e.g., a beep, chime, the words "time is up", etc.). In some embodiments, when the timer finishes counting down, the water dispensed from outlet 45 is automatically stopped. In other embodiments, the user can manually turn off the water using handle 20.

Figure 2C:
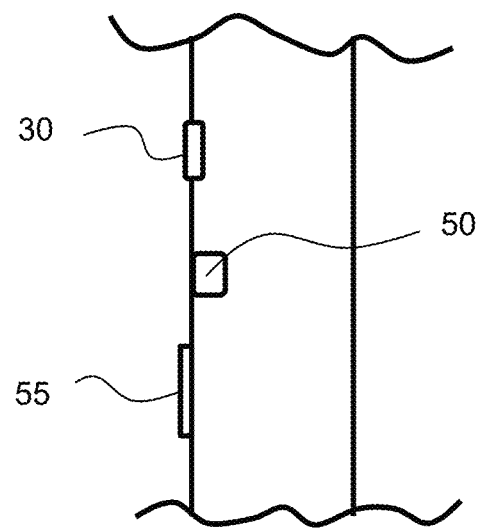
FIG. 2c is a fragmentary view of a faucet comprising an internal controller in accordance with some embodiments of the presently disclosed subject matter.

The timing sensor cooperates with controller 50 located internal or external to the faucet, as shown in FIG. 2c. Thus, the timing sensor is configured to send a detection signal to controller 50 when it detects that a user is within a set distance from the faucet (e.g., approaches the faucet or places his hands under the faucet). Alternatively, the timing sensor can be activated when a voice control is given by the user ("turn faucet on"). In response, the controller activates timer 55 which can then begin counting down. After the timer has fully counted down, it will reset or be deactivated. In the same way, timing sensor 30 can also detect when the user is no longer near the faucet. Particularly, when the timing sensor indicates that the user is no longer using the faucet, it can deactivate timer 55. The control module can be connected to the sensor and timer wirelessly or can use conventional connection elements (wires, leads, etc.).

Thus, a continuous feedback loop can be established between the timing sensor and the timer to detect when a user removes their hands from the faucet, thereby deactivating the timer. If the user removes their hands prematurely (e.g., prior to the completion of timer 55), the timer can optionally include a visual and/or auditory alert. For example, the timer screen can flash, the timer screen can include a visible message, and/or the timer can produce a sound (e.g., a tone or words) that indicate that the user's handwashing lasted for an insufficient amount of time. Optionally the faucet can then prompt the user to resume and finish or completely restart the handwashing process.

In some embodiments, faucet 10 is capable of tracking and monitoring individual users, such as the frequency of handwashing, the length of handwashing, and the like. In these embodiments, the user can provide individual identifying information through manual input, voice or facial recognition software, presenting/scanning a User ID card or other identification object, and the like. User identification data can include patient records, electronic medical records (EMR), or Electronic Health Record (EHR). Accordingly, the controller can be linked to a remote computer or server storing EMR or other user data.

The timer can receive power using any conventional mechanism, such as (but not limited to) a battery.

Figure 3A:
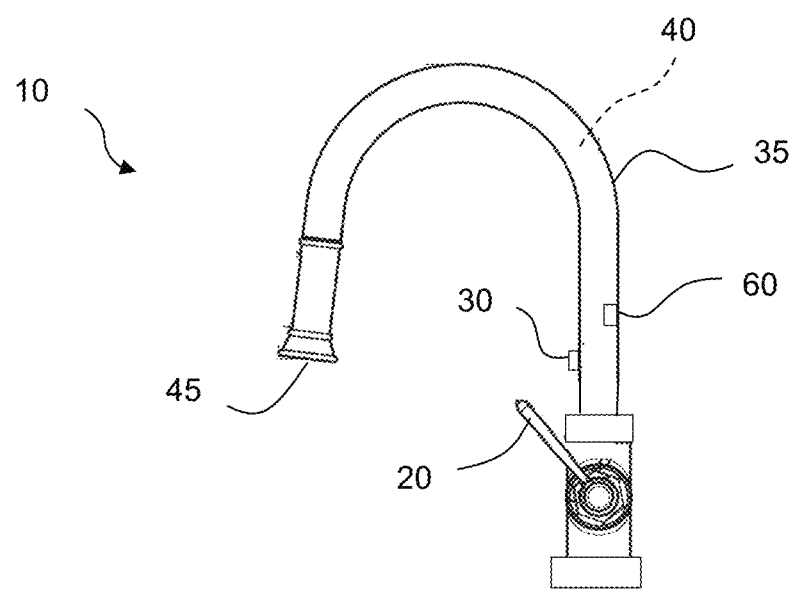
FIG. 3a is a side plan view of a faucet comprising an internal thermal sensor in accordance with some embodiments of the presently disclosed subject matter.

Faucet 10 further includes one or more thermal sensors 60 positioned within the interior passageway of the sensor, as shown in FIG. 3a. The term "thermal sensor" refers to any sensor configured detect the temperature of water that is traveling through the interior of the faucet, to be dispensed from outlet 45. Suitable thermal sensors can include (but are not limited to) infrared sensors, thermistors, thermocouplers, diode-type sensors, resistance temperature detector (RTD) sensor, and the like. Accordingly, the temperature of the water can be tracked to provide data on water environments that are conducive to bacterial growth, such as legionella. Legionella is a genus of gram negative, aerobic bacteria that is very common to aquatic warm water environments. Exposure to legionella (such as when a person inhales aerosols or other microscopic water droplets containing the bacteria) causes legionellosis.

In typical city water supply systems, the end devices for water delivery elements capable of dispersing the legionella bacteria include faucets. Specifically, the conditions that promote growth of the bacteria in water systems include stagnant water, a pH between 5 and 8, water temperatures between about 68-122° F., and the biofilm deposits in the pipe systems. It is therefore essential that hot and cold water systems be monitored for high quality water management and risk mitigation. Failure to do so can lead to severe outbreaks of legionella, extensive reputational damage, and huge fines.

Quarterly testing for legionella is often mandated for large facilities. In most cases, infections occur when systems have been left to operate outside of the suggested guidelines. Further, when water does not flow well, the resulting areas of stagnation encourage biofilm growth, reduce water temperatures to those favorable for legionella growth, and reduce levels of disinfectant. Thus, even though high temperatures have proven to be very successful for purging water systems of legionella, the bacteria have been found to survive in temperatures as high as 145° F. Further, construction, water main breaks, and changes in municipal water quality are all important factors that can affect water conditions. Therefore, quarterly testing may not be sufficient to protect employees and/or patients in many settings.

In some embodiments, the thermal sensor is triggered by initiation of timing sensor 30. In other embodiments, the thermal sensor is triggered by the movement of water through the interior of the faucet neck.

Figure 3B:
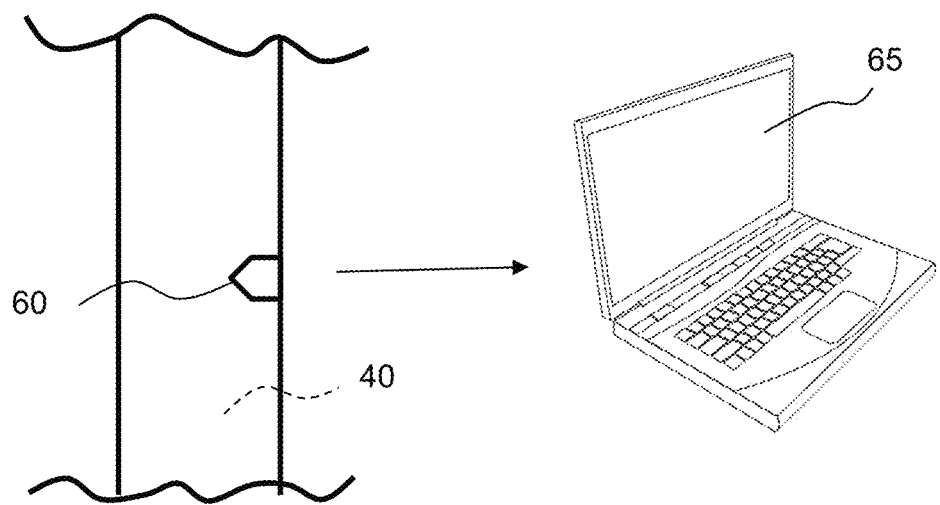
FIG. 3b is a fragmentary front plan view of a thermal sensor transmitting to a data receiving unit in accordance with some embodiments of the presently disclosed subject matter.

Thermal sensor 60 can therefore monitor the temperature of water flowing through faucet 10. The data can be transmitted to a central processing center 65 that compiles and tracks the data, as shown in FIG. 3b. The processing center can include one or more computers, phones, and other similar data receiving elements. Data can be stored locally in memory or remotely on a remote server or computer. In some embodiments, data stored in memory can be remotely accessible over a wireless communications system, as would be known in the art.

Figure 4:
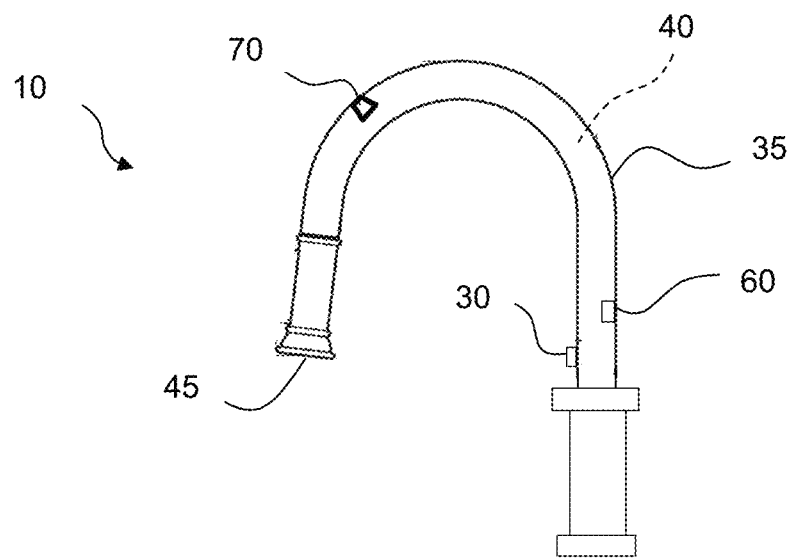
FIG. 4 is a side plan view of a faucet comprising a protein sensor in accordance with some embodiments of the presently disclosed subject matter.

In some embodiments, the interior of faucet neck 40 can further include one or more protein sensors 70 capable of detecting single protein molecules of a bacterium (e.g., legionella), as illustrated in FIG. 4. The protein sensor can therefore detect the levels of legionella present in running water that flows through the faucet. The protein sensors can be any conventional sensor capable of detecting protein levels, such as the use of bound carbon nanotubes and the like.

The protein sensor can be positioned anywhere within the interior 40 of faucet 10. For example, protein sensor 70 can be located adjacent to faucet outlet 45, at the opposing end of the faucet neck, or anywhere in between.

Similar to the thermal sensor, data received from protein sensor 70 can be transmitted and stored within central processing center 65 that compiles and tracks the data. For example, the central processing center can include one or more computers, phones, and the like. When information received by the central processing center meets a threshold level, such as when the water temperatures are conducive to the growth of legionella and/or a detectable amount of legionella is received, an alert can be transmitted to hospital staff and/or an administrator in charge of such information. For example, if the thermal sensor indicates that temperatures are suitable for the growth of legionella, the administrator can take further action, such as to assess the current water system, do additional testing, take ameliorative action, and the like. Similarly, if protein sensor 70 indicates a legionella protein level at or above a predetermined threshold limit, faucet 10 can be flagged. In addition, the water may be shut off or restricted until the level of legionella is reduced to an acceptable level.

Figure 5A:
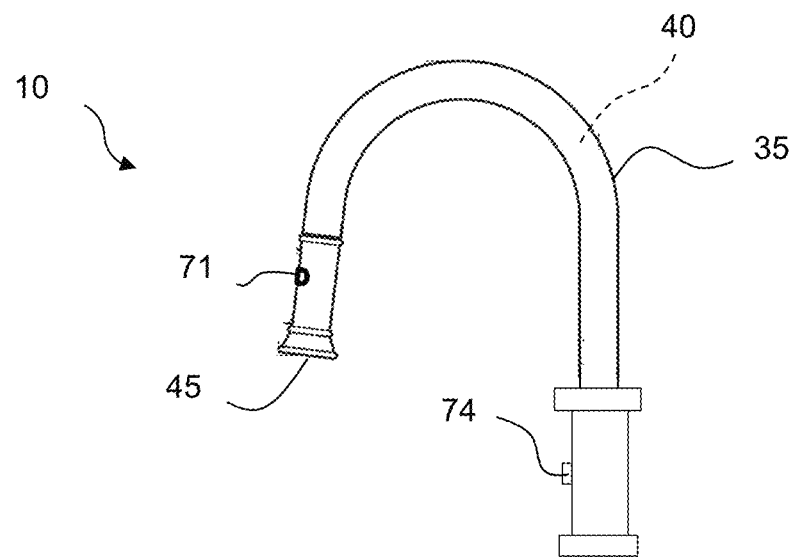
FIG. 5a is a side plan view of a faucet comprising a visible light fluorescence spectrometry element.
Figure 5B:
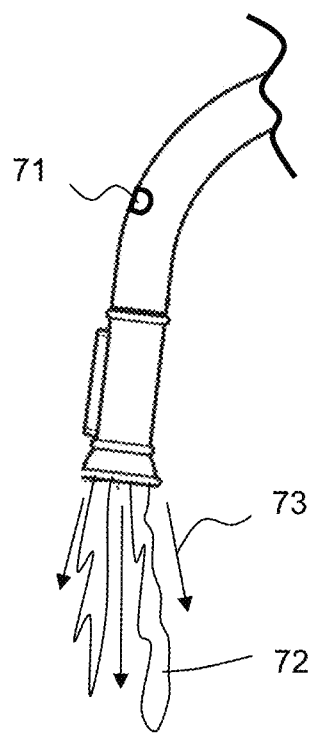
FIG. 5b is a side plan view of a faucet output comprising a visible light fluorescence spectrometry element in use.

In some embodiments, the interior of faucet 10 further includes a mechanism that enables the user to visualize dirt, harmful microorganisms, etc. present on their hands. For example, the interior of the faucet can include visible light fluorescent spectroscopy element 71, as shown in FIG. 5a. The term "fluorescent spectroscopy" refers to a method of qualitative and/or quantitative analysis of a surface using the characteristics and intensity of fluorescence generated by a substance under light (e.g., visible light) irradiation. "Visible light" refers to the visible spectrum of light (400-700 nanometers) because humans can see it. For example, the blue light range of the visible light spectrum has a wavelength of about 400-525 nanometers. When the water flow is initiated in the faucet, the interior of the faucet (and water flow 72 that exits from outlet 45) is illuminated with blue light 73. The light will therefore shine on a user's hands while they are washing using faucet 10, as shown in FIG. 5b. Harmful microorganisms (e.g., bacteria, viruses, mold, etc.) present on the user's hands will fluoresce in the blue light, allowing the user to visibly detect whether their hands are still contaminated. If the user does not detect the presence of any fluorescence, their hands are substantially free to microbial contamination (e.g., at least about 85, 90, 95, 99, or 99.9 percent free). However, if the user observes areas of fluorescence on their hands, it is an indication that microbial contaminants are still present on their hands and they should wash for a longer period of time.

The fluorescent spectroscopy element can include a light source to illuminate a detection zone below the output of the faucet to thereby shine on a user's hands while washing. The light source can take any form, such as one or more bulbs (LEDs), mercury vapor lights, fluorescent lamps, emitters, or any other source capable of generating light in the appropriate range. The light source is such that the excitation wavelength or wavelengths are from the visible section of the electromagnetic spectrum, and thus would pose the least threat of injury to the user. In some embodiments, the area of interest (the hands) would be illuminated with light from the blue portion of the electromagnetic spectrum with an excitation wavelength of about 400-440 nm. Each light source element has a wavelength sufficient to illuminate a harmful microorganism, such as bacteria, viruses, molds, fungi, or combinations thereof. As a result, fluorescent light emissions are then able to be detected on the user's hands, indicating the presence of a microbial contaminant on the user's hands.

In some embodiments, the faucet can include proximity sensor 74 to ensure that a user's hands are present below the faucet prior to the light source being activated. Specifically, the sensor can provide for electronic control of the light emissions, such that light will not be emitted from the light source unless the user's hands are below the faucet output and/or before water is funning from the faucet. Such use of a distance sensor and affiliated circuitry provides for increased safety to the user and others in the vicinity in that the light emission will not be activated except when there is an object present below output 45, thus providing the increased benefit of reducing any unintended and thus unnecessary exposure to the light source. Object sensing technologies can include (but are not limited to) infrared and ultrasonic proximity-sensing or photo-electric technologies. The circuitry for creating such an object safety mechanism is also well known in the art.

In some embodiments, the fluorescent spectroscopy element can be positioned anywhere within the interior of faucet neck 40, such as (but not limited to) adjacent to the faucet outlet.

Figure 6:
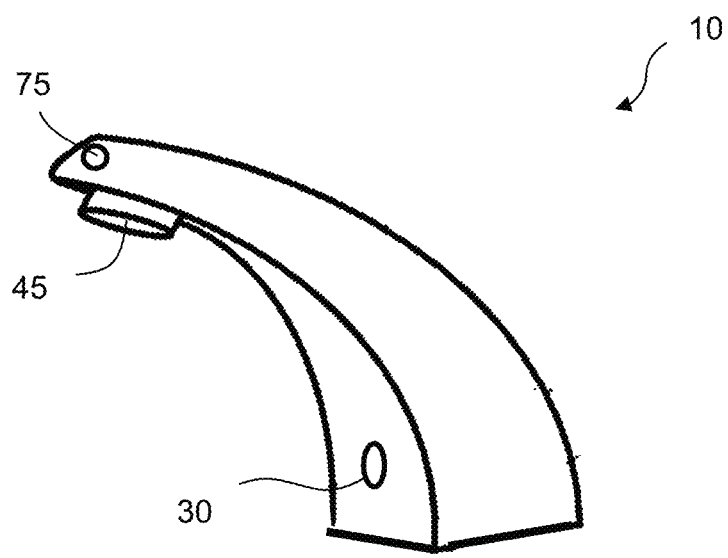
FIG. 6 is a perspective view of a faucet comprising a transmitter in accordance with some embodiments of the presently disclosed subject matter.

Faucet 10 can further include one or more optional features. For example, the disclosed faucet can include one or more transmitters 75 that allow music to be played for a predetermined time, such as while the user washes their hands, as shown in FIG. 6. The transmitter can act as a speaker in some embodiments. Thus, when motion sensor 30 is triggered, transmitter 75 can be activated to initiate the playing of music (or any other auditory element, such as jokes, facts, or other pre-recorded elements). When the music stops, it is an indication that the appropriate amount of time for hand washing has passed (e.g., 20-30 seconds). The transmitter can be positioned at any location on the faucet.

In embodiments wherein the faucet is interactive, the transmitters can be used to transmit information to the user, such as (but not limited to) how much time remains in timer 50, that the timer has elapsed, etc.

Figure 7:
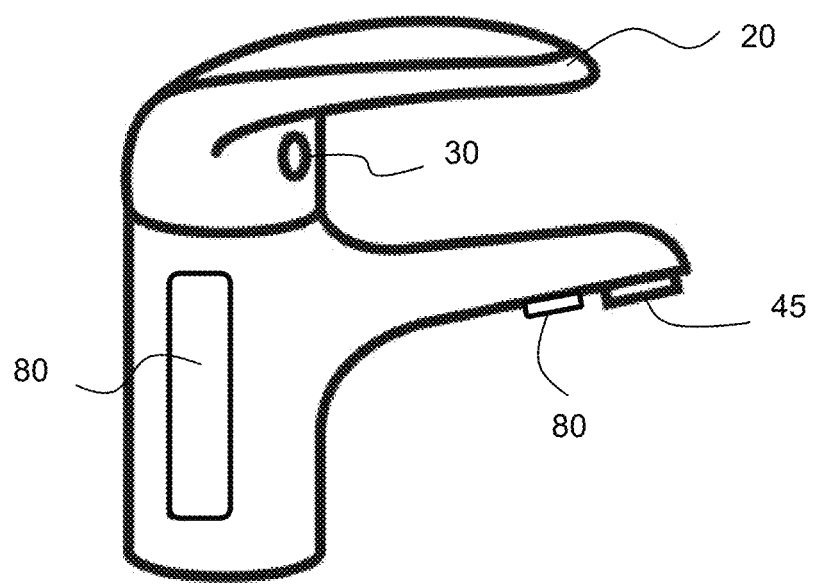
FIG. 7 is a perspective view of a faucet comprising one or more lights in accordance with some embodiments of the presently disclosed subject matter.

In addition, the disclosed faucet can be configured with one or more lights that flash or shine for a predetermined amount of time after the motion sensor is activated. A shown in FIG. 7, lights 80 can be positioned at any location on the faucet, such as the faucet exterior, the faucet outlet, or combinations thereof. Any number of lights 80 can be used. The lights can comprise any conventional element, such as light emitting diodes, bulbs, fiber optics, light pipes, luminescent materials, and the like.

Advantageously, faucet 10 is designed to work with a variety of sink configurations. For example, the faucet can be adapted to its environment to eliminate unintended activations caused by users walking past the faucet and the like.

Further, faucet 10 can be highly customized to a particular environment and user. Thus, the faucet can provide audio/video messages in any number of languages and can have context-specific references to the establishment where the faucet is used. For example, in a hospital setting, the audio/video messages can reference specific hospital policies, federal and local regulatory guidelines (e.g., U.S. Occupational Safety and Health Administration (OSHA), Centers for Disease Control and Prevention (CDC), Food and Drug Administration (FDA), etc.), and bylaws. The disclosed faucet can therefore be used in a variety of settings, such as restrooms, hospitals, laboratories, and kitchens.

Figure 8:
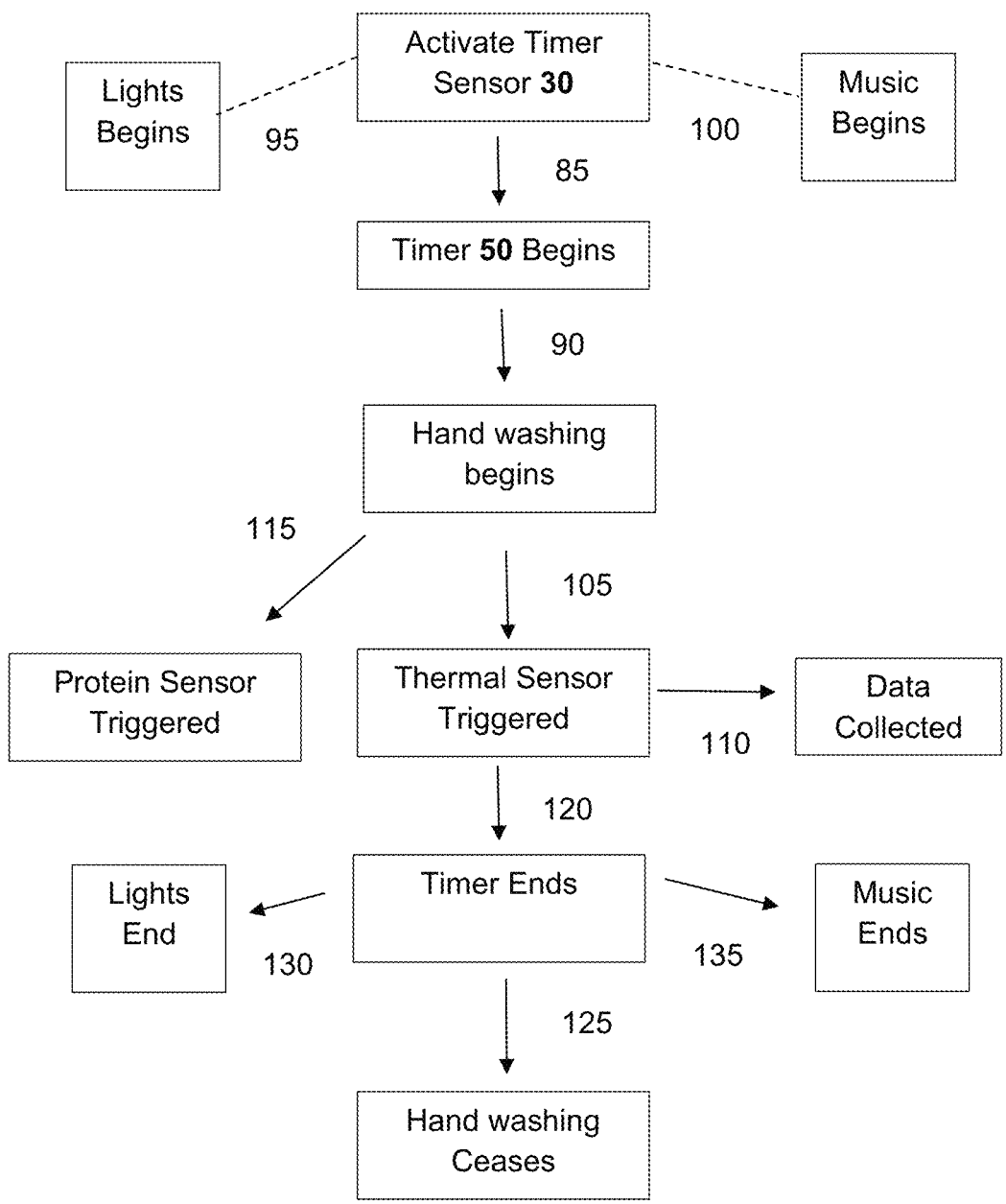
FIG. 8 is a schematic illustrating one embodiment of using a faucet in accordance with some embodiments of the presently disclosed subject matter.

FIG. 8 is a schematic illustrating one method of using the disclosed faucet. Particularly, timing sensor 30 is activated by a user at step 85. In some embodiments, the timing sensor is motion-activated such that when a user approaches the faucet, it is initiated. In other embodiments, the sensor is voice-activated such that when the user speaks, the sensor is triggered. In still other embodiments, the first sensor can be light activated, such as when a bathroom light is enabled and the user enters a bathroom. It is envisioned that a single sensor can have the capability to be motion activated, voice activated, and/or light activated.

After the timing sensor is activated, timer 50 begins to count down for a predetermined time period. For example, the timer can count for 20 seconds, the recommended amount of time for hand washing.

Optionally, activation of sensor 30 can also trigger music to play and/or lights to turn on for a predetermined amount of time as shown in steps 95, 100.

The user then initiates dispensing of the water by manipulating the handles 20 (e.g., adjusting flow, temperature). In some embodiments, the flow of water automatically begins when the first sensor is triggered (e.g., the faucet is hands-free). The user then begins hand washing at step 90. As water is flowing through the faucet, thermal sensor 60 measures the temperature of the water at step 105 to determine whether conditions are favorable for the growth of bacteria (such as legionella). The data is stored and/or reported to track conditions suitable for bacterial growth at step 110.

Protein sensor 70 can also take readings when the water is flowing at step 115. The readings measure the protein of one or more bacteria, as described above. The data is reported and can be transmitted for study or further action.

At the end of the predetermined time period, the timer stops at step 120. The user is thereby informed that the appropriate amount of time for hand washing has elapsed, and hand washing ceases at step 125. In addition, the optional music and lights will also stop at steps 130, 135.

Faucet 10 offers many advantages over prior art faucets. Particularly, the disclosed faucet allows a user to wash their hands easily and effectively for the appropriate amount of time to reduce the spread of infection.

The disclosed faucet can be easily used by a wide variety of users, including children and the elderly.

The faucet promotes hand washing in children and others that may not effectively wash their hands by providing a timer, lights, and/or music.

Advantageously, faucet 10 can be used by the visual and hearing impaired. For example, activation sensor can tell a visually impaired user when to begin washing their hands and how much time is left. Similarly, the timer can notify a hearing-impaired user how much time remains.

In addition, the faucet enables the temperature of the water to be monitored to determine whether conditions are optimal for the growth of legionella and other harmful bacteria.

Further, faucet 10 can include a sensor that detects specific protein indicators that indicate the presence of legionella. In this way, spread of the bacteria can be eliminated or reduced quickly and effectively.

The disclosed faucet is also capable of hands-free use, which reduces or eliminates the transfer of harmful microorganisms between users.

In addition, data can be compiled, allowing a facility to track user hand washing statistics, such as the number of times hands have been washed, the time of hand washing, and the like. Further, the water conditions can be recorded and tracked, as well as the presence of legionella-indicating proteins. In this way, trends can be recorded and used for study.

As described above, although a preferred embodiment of the present invention has been described for illustrative purposes, those skilled in the art will appreciate that various modifications, additions and substitutions are possible, without departing from the scope and spirit of the invention as disclosed in the accompanying claims.

What is claimed is:

1. A faucet comprising:
   a neck defined by an interior passageway configured to allow the flow of water therethrough and an outlet through which water exits the faucet;
   a timing sensor triggered by a user's approach to the faucet;

a timer configured to run for a predetermined amount of time, wherein the timer is initiated by the triggering of the timer sensor; and a visible light fluorescence spectrometer element configured to illuminate the area below the faucet outlet with blue visible light, thereby illuminating one or more microbial contaminants on an object positioned below the faucet outlet.

2. The faucet of claim 1, wherein the timer sensor is selected from one or more motion sensors, heat sensors, light sensors, and/or voice activated sensors.

3. The faucet of claim 1, wherein the predetermined amount of time is about 20 seconds.

4. The faucet of claim 1, wherein the timer provides a visual countdown, an audible countdown, or both.

5. The faucet of claim 1, further comprising one or more thermal sensors configured to detect the temperature of water passing through the interior passageway of the neck.

6. The faucet of claim 5, wherein the thermal sensor is selected from one or more infrared sensor, thermistor, thermocouple, diode sensor, or resistance temperature detector.

7. The faucet of claim 5, wherein the one or more thermal sensors are powered on by the presence of water, the timing sensor, or both.

8. The faucet of claim 5, wherein data produced by the thermal sensor is transmitted to a central processing center.

9. The faucet of claim 1, further including one or more lights that are initiated by the triggering of the timing sensor.

10. The faucet of claim 1, further comprising a transmitter that projects an audible message, initiated by the triggering of the timing sensor.

11. A method of indicating to a user the proper amount of time to wash their hands, the method comprising:

initiating the timing sensor of the faucet of claim 1;

initiating water flow from the faucet outlet, whereby the user washes their hands until the timer indicates that a predetermined time has elapsed;

wherein the proper amount of time to wash their hands has elapsed.

12. The method of claim 11, wherein the predetermined amount of time is about 20 seconds.

13. The method of claim 11, wherein the timer provides a visual countdown, an audible countdown, or both.

14. The method of claim 11, wherein the timer provides an indicator to the user when the predetermined amount of time has elapsed.

15. A method of illuminating the presence of one or more microbial contaminants on an object, the method comprising:

positioning the object below an outlet of the faucet of claim 1;

initiating the visible light fluorescence spectrometer element to illuminate the area below the faucet outlet with blue visible light;

whereby one or more microbial contaminants on an object positioned below the faucet outlet are illuminated if present.

16. The faucet of claim 1, wherein the timer is positioned within the neck of the faucet or attached to an external surface of the faucet neck.

17. The faucet of claim 1, comprising a plurality of timing sensors.

18. The faucet of claim 1, wherein the faucet neck has a length of about 1-20 inches.

19. The faucet of claim 1, wherein the faucet is constructed from stainless steel, bronze, copper, steel, galvanized steel, ceramics, polyvinyl chloride, polyethylene, polybutylene, or polypropylene.

20. The faucet of claim 1, wherein the blue visible light has a wavelength of about 400-525 nanometers.

* * * * *